United States Patent
Rezai et al.

(10) Patent No.: US 9,162,073 B2
(45) Date of Patent: Oct. 20, 2015

(54) METHOD FOR TREATING ERECTILE DYSFUNCTION

(75) Inventors: Ali R. Rezai, Shaker Heights, OH (US); Roy K. Greenberg, Bratenahl, OH (US); Milind Deogaonkar, Broadview Heights, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 1325 days.

(21) Appl. No.: 12/934,930

(22) PCT Filed: May 30, 2008

(86) PCT No.: PCT/US2008/065188
§ 371 (c)(1),
(2), (4) Date: Sep. 27, 2010

(87) PCT Pub. No.: WO2008/150941
PCT Pub. Date: Dec. 11, 2008

(65) Prior Publication Data
US 2011/0077458 A1    Mar. 31, 2011

Related U.S. Application Data

(60) Provisional application No. 60/932,212, filed on May 30, 2007.

(51) Int. Cl.
*A61N 1/36* (2006.01)
*A61N 1/378* (2006.01)
(Continued)

(52) U.S. Cl.
CPC ............... *A61N 1/3787* (2013.01); *A61F 2/26* (2013.01); *A61F 2/82* (2013.01); *A61N 1/0551* (2013.01); *A61N 1/3605* (2013.01); *A61N 1/36007* (2013.01); *A61N 1/36107* (2013.01); *A61F 2250/0001* (2013.01); *A61N 1/37205* (2013.01)

(58) Field of Classification Search
CPC ............ A61N 1/36007; A61N 1/3605; A61N 1/36107; A61N 1/37205; A61F 2/26
USPC .................................................... 607/39, 143
See application file for complete search history.

(56) References Cited

U.S. PATENT DOCUMENTS 6,231,516 B1    5/2001    Keilman et al.
2002/0026228 A1    2/2002    Schauerte
(Continued)

FOREIGN PATENT DOCUMENTS

WO    WO-2006/041881 A2    4/2006
WO    WO-2006/091611 A1    8/2006

*Primary Examiner* — Tammie K Heller
(74) *Attorney, Agent, or Firm* — Tarolli, Sundheim, Covell & Tummino LLP (57) ABSTRACT

A method for treating erectile dysfunction in a subject includes providing an expandable support member for engaging a wall of a blood vessel. The expandable support member includes at least one electrode connected with the expandable support member and arranged to selectively deliver electric current to modulate the autonomic nervous system (ANS). The expandable support member includes and an insulative material attached to at least a portion of the expandable support member for isolating blood flowing through the vessel from the electric current delivered by the at least one electrode. The expandable support member is implanted intravascularly so that at least a portion of the expandable support member is positioned substantially adjacent a desired location where modulation of the ANS is effective to improve erectile function. After implanting the expandable support member, electric current is delivered to the at least one electrode to effect a change in the ANS.

21 Claims, 7 Drawing Sheets

(51) Int. Cl.
*A61F 2/26* (2006.01)
*A61F 2/82* (2013.01)
*A61N 1/05* (2006.01)
*A61N 1/372* (2006.01)

(56) References Cited

U.S. PATENT DOCUMENTS

| | | |
|---|---|---|
| 2002/0055761 A1 | 5/2002 | Mann et al. |
| 2004/0019364 A1 | 1/2004 | Kieval et al. |
| 2004/0073268 A1 | 4/2004 | Zappala |
| 2004/0088021 A1 | 5/2004 | Cameron et al. |
| 2005/0209651 A1 | 9/2005 | Cameron et al. |
| 2005/0240229 A1 | 10/2005 | Whitehurst et al. |
| 2006/0085046 A1* | 4/2006 | Rezai et al. ............ 607/40 |
| 2006/0129028 A1 | 6/2006 | Krakousky |
| 2006/0149345 A1 | 7/2006 | Boggs, II et al. |
| 2006/0183970 A1 | 8/2006 | Zappala |
| 2006/0190046 A9 | 8/2006 | Gerber |
| 2006/0195152 A1 | 8/2006 | Gerber |

* cited by examiner

Fig. 7 ically to an implantable stimulation device and related method for delivering intravascular electrical stimulation as a therapy for erectile dysfunction and other sexual disorders.

METHOD FOR TREATING ERECTILE DYSFUNCTION

RELATED APPLICATION

This application claims priority from U.S. Provisional Patent Application Ser. No. 60/932,212, filed on May 30, 2007, the subject matter of which is incorporated herein by reference.

TECHNICAL FIELD

The present invention relates generally to implantable stimulation devices and methods, and more particularly to an implantable stimulation device and related method for delivering intravascular electrical stimulation as a therapy for erectile dysfunction and other sexual disorders.

BACKGROUND OF THE INVENTION

Recent estimates suggest that the number of U.S. men with erectile dysfunction (ED) may be near 10 to 20 million, and inclusion of individuals with partial ED increases the estimate to about 30 million. ED has a number of etiologies, including neuropathy and vascular disease. The male erectile response is initiated by the action of neurons, or nerve cells (i.e., neuronal action), and is maintained by a complex interplay between events involving blood vessels (i.e., vascular events) and events involving the nervous system (i.e., neurological events).

It is parasympathetic neuronal action that initiates the male erectile response. Specifically this parasympathetic input originates from the pelvic splanchnic nerve plexus. The pelvic splanchnic nerve plexus is comprised of branches from the second, third, and fourth sacral nerves that intertwine with the inferior hypogastric plexus, which is a network of nerves in the pelvis. The cavernous nerves are derived from the pelvic splanchnic nerves, via the prostatic plexus, and supply parasympathetic fibers to the corpora cavernosa and corpus spongiosum, the spongy tissues in the penis that are engorged with blood during an erection. The corpora cavernosa are two paired tissue bodies that lie dorsally in the penis, while the corpus spongiosum is located ventrally and surrounds the urethra. The corpus spongiosum expands at the terminal end to form the glans penis. These erectile tissues are comprised of venous spaces lined with epithelial cells separated by connective tissue and smooth muscle cells.

Parasympathetic activity allows erection by relaxation of the smooth muscle and dilation of the helicine arteries, which are arteries found in the erectile tissue of the penis. The dilation of the arteries causes greatly increased blood flow through the erectile tissue, which leads to expansion of the corpora cavernosa and the corpus spongiosum. As the corpora cavernosa and the corpus spongiosum expand, the venous structures draining the penis are compressed against the fascia surrounding each of the erectile tissues. This vein-obstruction process is referred to as the corporal veno-occlusive mechanism.

Conversely, sympathetic innervation from the hypogastric nerves and/or certain nerves of the inferior hypogastric plexus, which derive from the sympathetic ganglia, inhibit parasympathetic activity and cause constriction of the smooth muscle and helicine arteries, making the penis flaccid. The flaccid state is maintained by continuous sympathetic (alpha-adrenergic) nervous system stimulation of the penile blood vessels and smooth muscle.

ED has a number of causes, both physiological and psychological, and in many patients the disorder may be multifactorial. Several causes are essentially neurological in origin. Damage to the spinal cord may produce varying degrees of erectile failure depending on the location and severity of the damage. Damage to the pathways used by the autonomic nervous system to innervate the penis may interrupt "psychogenic" erection initiated by the central nervous system. Damage to somatic nervous pathways may impair reflexogenic erections and may interrupt tactile sensation needed to maintain psychogenic erections. Not only do traumatic lesions affect erectile ability, but disorders leading to peripheral neuropathy may impair neuronal innervation of the penis or of the sensory afferents. The endocrine system itself, particularly the production of androgens, appears to play a role in regulating sexual interest, and may also play a role in erectile function. Additionally, ED is a common complication of prostate surgery, such as prostatectomy (surgical removal of all or part of the prostate).

Various stimulation devices and medications have been proposed for treating ED; however, such approaches present significant drawbacks. For example, treatment of ED with medications results in undesirable side effects. Additionally, stimulation methods are highly invasive and offer only short-term improvement of erectile function.

SUMMARY OF THE INVENTION

In one aspect of the present invention, a method is provided for treating erectile dysfunction in a subject. One step of the method includes providing an expandable support member for engaging a wall of a blood vessel. The expandable support member includes at least one electrode connected with the expandable support member and arranged to selectively deliver electric current to modulate the autonomic nervous system (ANS). The expandable support member also includes and an insulative material attached to at least a portion of the expandable support member for isolating blood flowing through the vessel from the electric current delivered by the at least one electrode. The expandable support member is implanted intravascularly so that at least a portion of the expandable support member is positioned substantially adjacent a desired location where modulation of the ANS is effective to improve erectile function. After implanting the expandable support member, electric current is delivered to the at least one electrode to effect a change in the ANS.

In another aspect of the present invention, a method is provided for treating neurogenic erectile dysfunction in a subject. One step of the method includes providing an expandable support member for engaging a wall of a blood vessel. The expandable support member includes at least one electrode connected with the expandable support member and arranged to selectively deliver electric current to modulate the ANS. The expandable support member also includes an insulative material attached to at least a portion of the expandable support member for isolating blood flowing through the vessel from the electric current delivered by the at least one electrode. After determining the location of at least one lesion causative of neurogenic erectile dysfunction in the subject the expandable support member is implanted intravascularly at a desired location distal from the at least one lesion so that at least a portion of the expandable support member is positioned substantially adjacent a desired location where modulation of the ANS is effective to improve erectile function. Upon implantation of the expandable support member, electric current is delivered to the at least one electrode to effect a change in the ANS.

In another aspect of the present invention, a method is provided for treating erectile dysfunction in a subject. One step of the method includes providing an expandable support member for engaging a wall of a blood vessel. The expandable support member includes at least one electrode being connected with the expandable support member and arranged to selectively deliver electric current to modulate the ANS. The expandable support member also includes at least one wireless module capable of receiving electrical energy for deliver to the at least one electrode. The expandable support member is implanted intravascularly so that at least a portion of the expandable support member is positioned substantially adjacent a desired location where modulation of the ANS is effective to improve erectile function. After implantation, electric current is delivered to the at least one wireless module such that the electric current is delivered to the at least one electrode to effect a change in the ANS.

BRIEF DESCRIPTION OF THE DRAWINGS

The foregoing and other features of the present invention will become apparent to those skilled in the art to which the present invention relates upon reading the following description with reference to the accompanying drawings, in which.

DETAILED DESCRIPTION

Figure 1:
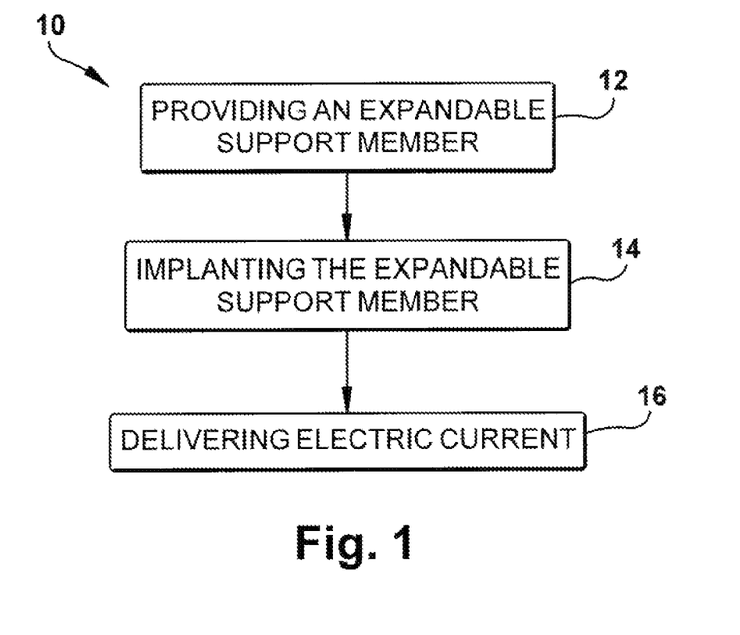
FIG. 1 is a process flowchart illustrating a method for treating erectile dysfunction in a subject according to the present invention.

The present invention relates generally to implantable stimulation devices and methods, and more particularly to an implantable stimulation device and related method fir delivering intravascular electrical stimulation as a therapy for erectile dysfunction (ED) and other sexual disorders. As representative of the present invention, FIG. 1 illustrates a method 10 for treating ED or impotence in a subject. Throughout the present application, the method 10 will be described with reference to treating ED generally. It will be appreciated, however, that the method 10 is not limited to treating ED of any one particular etiology. Additionally, it should be appreciated that the present invention may be used to treat other sexual disorders, such as anorgasmia.

Unless otherwise defined, all technical terms used herein have the same meaning as commonly understood by one of ordinary skill in the art to which the present invention pertains.

In the context of the present invention, the term "autonomic nervous system" or "ANS" refers to the part of the peripheral nervous system that controls homeostasis and adjusts or modifies some physiological functions in response to stress. The ANS helps to regulate blood pressure and vessel size, the heart's electrical activity and ability to contract, and the bronchium's diameter in the lungs. Additionally, the ANS regulates the movement and work of the stomach, intestine and salivary glands, the secretion of insulin, and urinary and sexual functions. The ANS acts through a balance of its two components, the sympathetic nervous system (SNS) and the parasympathetic nervous system (PNS).

As used herein, the term "parasympathetic nervous system" or "PNS" refers to the part of the ANS originating in the brain stem and the lower part of the spinal cord that, in general, inhibits or opposes the physiological effects of the SNS (e.g., stimulating digestive secretions, slowing the heart, constricting the pupils, and dilating blood vessels).

As used herein, the term "sympathetic nervous system" or "SNS" refers to the part of the ANS originating in the thoracic and lumbar regions of the spinal cord that generally inhibits or opposes the physiological effects of the PNS.

As used herein, the term "desired location" refers to a desired anatomical location where modulation of the ANS is effective to improve erectile function. The desired location can comprise a variety of anatomical locations, including intraluminal and extraluminal locations innervated by at least one nerve. For example, the desired location can comprise an intravascular or extravascular location innervated by at least one nerve. Examples of desired locations according to the present invention can include locations adjacent to and or innervated by the sympathetic chain, the superior hypogastric plexus, a hypogastric nerve, the hypogastric plexus, a sacral sympathetic nerve, and/or the inferior hypogastric plexus. Desired locations contemplated by the present invention are also illustrated in FIG. 2 and FIGS. 4-6, and are described in further detail below.

As used herein, the term "erectile dysfunction" or "ED" refers to any and all types of erectile dysfunction, including vasculogenic, neurogenic, endocrinologic and psychogenic impotence, Peyronie's syndrome, premature ejaculation, and any other condition, disease, or disorder, regardless of cause or origin, which interferes with at least one of the three phases of human sexual response, i.e., desire, excitement and orgasm.

As used herein, the term "impotence" is used here in its broadest sense to indicate a periodic or consistent inability to achieve or sustain an erection of sufficient rigidity for sexual intercourse.

As used herein, the term "subject" refers to any warm-blooded organism including, but not limited to, human beings, pigs, rats, mice, dogs, goats, sheep, horses, monkeys, apes, rabbits, cattle, etc.

Figure 2:
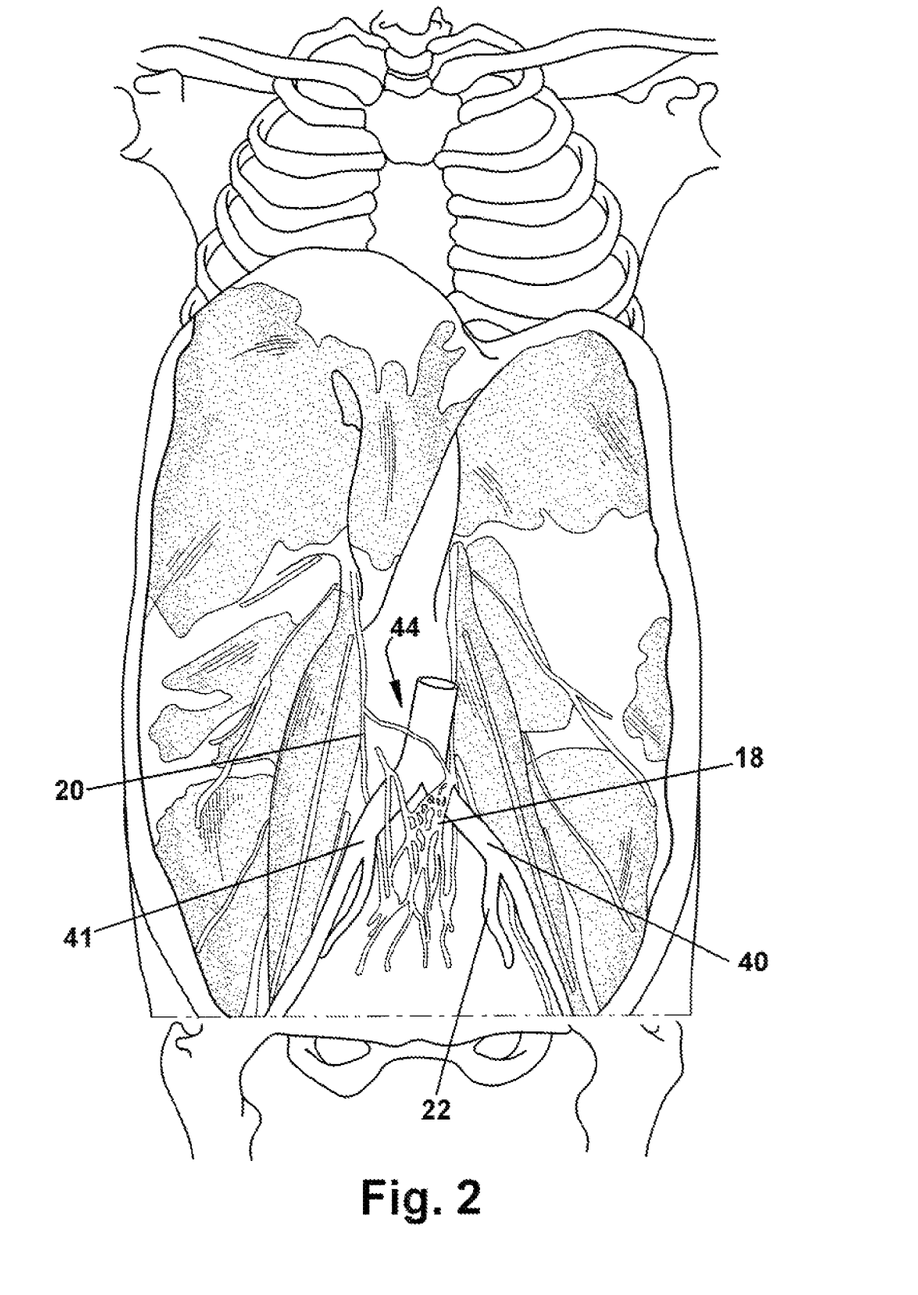
FIG. 2 is a perspective view of an abdominal cavity showing the abdominal aorta and hypogastric plexus.

A brief discussion of the neurophysiology is provided to assist the reader with understanding the present invention. FIG. 2 shows the abdominal cavity and depicts the sympathetic and parasympathetic fibers of the ANS that are responsible for innervation of the male reproductive organs (not shown). The parasympathetic input that initiates the male erectile response originates in the pelvic splanchnic nerve plexus (not shown). The pelvic splanchnic nerves (not shown) are comprised of parasympathetic branches from the second, third, and fourth sacral nerves (not shown) that intertwine with the inferior hypogastric plexus (not shown). The greater cavernous nerve (not shown) and the lesser cavernous nerve (not shown) are derived from the pelvic splanchnic nerves, via the prostatic plexus (not shown), and carry the parasympathetic input to the corpora cavernosum (not shown) and corpus spongiosum (not shown). Sympathetic input from the inferior hypogastric plexus and its branches, which derive from the hypogastric plexus 18 and the sympathetic ganglia 20, inhibit erection.

The parasympathetic signals carried to the corpora cavernosum and corpus spongiosum cause relaxation of smooth muscle surrounding the arteries and arterioles of the penis and dilation of the arteries and arterioles of the penis. The dilation of the arteries and arterioles causes increased blood flow through the erectile tissue, which leads to expansion of the corpora cavernosa and the corpus spongiosum. Due to this expansion, the venous structures draining the penis are compressed against the corpora cavernosum's tunica albuginea (not shown) and the corpus spongiosum's tunica albuginea (not shown). Thus, the outflow of blood is restricted and the internal pressure increases.

The arteries bringing blood to the cavernous spaces of the penis are the deep arteries of the penis and branches from the dorsal arteries of the penis. The internal iliac artery 22, after giving off a superior gluteal artery (not shown) and an inferior gluteal artery (not shown), forms the internal pudendal artery (not shown). The internal pudendal artery branches into the deep arteries of the penis and the dorsal arteries of the penis. The dorsal arteries supply blood to the erectile tissue of the glans penis. The deep arteries supply the two corpora cavernosa. Some of these arteries assume a tendril-like appearance, forming convoluted and somewhat dilated vessels referred to as helicine arteries (not shown). The helicine arteries end in small capillary branches supplying the cavernous spaces, and are most abundant in the back part of the corpora cavernosa.

The blood from the cavernous spaces is returned by a series of vessels, some of which emerge in considerable numbers from the base of the glans penis and converge on the dorsum of the organ to form the deep dorsal vein (not shown). Others travel along the upper surface of the corpora cavernosa to join the deep dorsal vein (not shown), while some emerge from the under surface of the corpora cavernosa and wind around the sides of the corpora cavernosa to end in the deep dorsal vein. A number of veins travel separate from the deep dorsal vein and exit at the base of the penis.

FIG. 1 is a process flowchart illustrating a method 10 for treating ED in a subject. At 12, an expandable support member 24 (FIG. 3) is provided for engaging a wall of a blood vessel. The expandable support member 24 is constructed as described in U.S. patent application Ser. No. 11/641,331, which is hereby incorporated by reference in its entirety.

Figure 3:
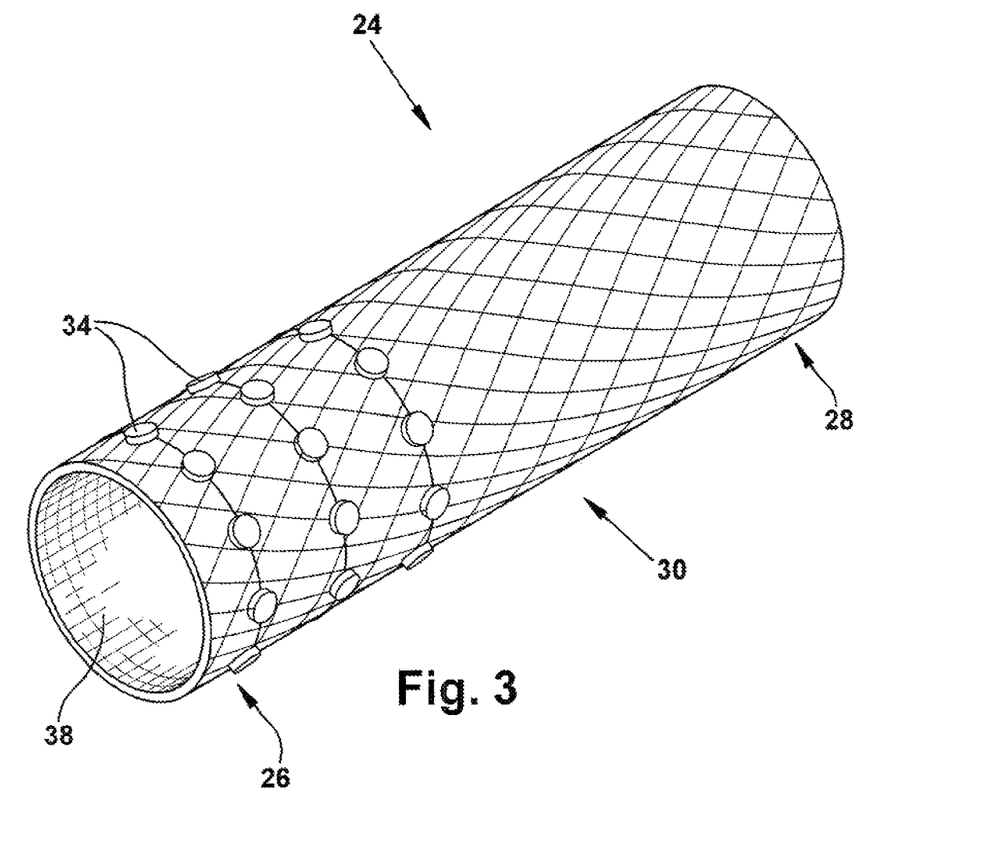
FIG. 3 is a perspective view of an implantable expandable support member constructed in accordance with the present invention.

Briefly, the expandable support member 24 includes oppositely disposed first and second end portions 26 and 28 and a main body portion 30 extending between the end portions. The structure of the expandable support member 24 may be a mesh, a zigzag wire, a spiral wire, an expandable stent, or other similar configuration that allows the expandable support member to be collapsed and expanded. The expandable support member 24 can be comprised of a material having a high modulus of elasticity, including, for example, cobalt-nickel alloys (e.g., Elgiloy), titanium, nickel-titanium alloys (e.g., cobalt-chromium alloys (e.g., Stellite), nickel-cobalt-chromium-molybdenum alloys (e.g., MP35N) graphite, ceramic stainless steel, and hardened plastics. The expandable support member 24 may also be made of a radio-opaque material or include radio-opaque markers (not shown) to facilitate fluoroscopic visualization.

The flexible and expandable properties of the expandable support member 24 facilitate percutaneous delivery of the expandable support member, while also allowing the expandable support member to conform to a portion of a blood vessel. An expanded configuration of the expandable support member 24 is shown in FIG. 3. In the expanded configuration, the expandable support member 24 has a circular cross-sectional shape for conforming to the circular cross-sectional shape of a blood vessel lumen. By conforming to the shape of a blood vessel lumen, the expanded configuration of the expandable support member 24 facilitates movement of the blood flow therethrough while also maintaining lumen patency.

Figure 5:
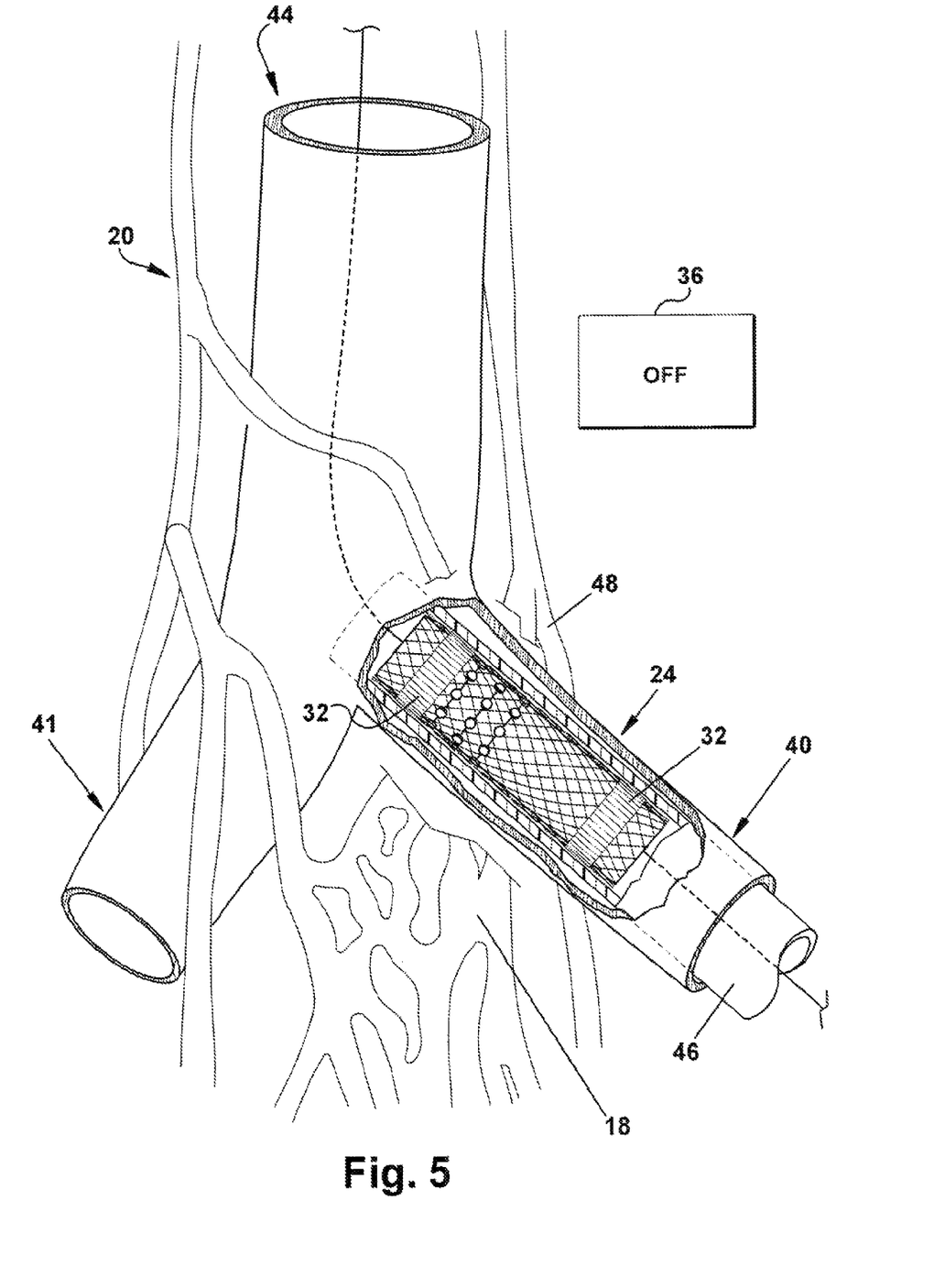
FIG. 5 is a perspective view showing the expandable support member of FIG. 3 being inserted into the left femoral artery.

At least one constraining band 32 (FIG. 5) may be placed around the circumference of the expandable support member 24 to maintain the expandable support member in the collapsed configuration. As shown in FIG. 5, the constraining bands 32 may comprise sutures, for example, and may be placed around the circumference of the expandable support member 24 as needed. Removal of the constraining bands 32 allows the expandable support member 24 to self-expand and obtain the expanded configuration. Where the constraining bands 32 comprise sutures, for example, the sutures may be manually broken or alternatively, broken by the radial force generated when the expandable support member 24 self-expands. It will be appreciated that the constraining bands 32 may comprise any other type of material capable of being selectively modified. For example, the constraining bands 32 may be made of a shape memory alloy, such as Nitinol, which can be selectively modified (i.e., expanded) by delivering energy (e.g., thermal energy) to allow the expandable support member 24 to obtain the expanded configuration.

The expandable support member 24 (FIG. 3) also includes at least one electrode 34 for delivering an electric current to a desired location. As shown in FIG. 3, the electrodes 34 have a flat, disc-like shape and are radially disposed about the circumference of the expandable support member 24 in a multi-electrode array configuration. It will be appreciated, however, that the electrodes 34 may have any shape and size, including, for example, a triangular shape, a rectangular shape, an ovoid shape, and/or a band-like shape (e.g., a split band configuration), and are not limited to the shapes and sizes illustrated in FIG. 3. The electrodes 34 may be configured so that the expandable support member 24 has a unipolar construction (FIG. 3) using the surround tissue as ground or, alternatively, a bipolar construction (not shown) using leads connected to either end of the expandable support member. The electrodes 34 may be made of any material capable of conducting an electrical current, such as platinum, platinum-iridium, or the like.

As shown in FIG. 3, the electrodes 34 can extend around only a portion of the expandable support member 24, such as the first end portion 26, in a radial fashion. Alternatively, the electrodes 34 may extend around only a portion or the entire circumference of the expandable support member 24 in a sinusoidal or helical fashion (not shown) or alternatively, the entire length of the expandable support member may be covered with the electrodes.

To facilitate focal delivery of electrical energy to a desired location, the electrodes 34 may wrap around the expandable support member 24 any number of times to establish a desired electrode contact and coverage. Additionally or optionally, the entire surface area of the electrodes 34 may be conductive or, alternatively, only a portion of the surface area of the electrodes may be conductive. By modifying the conductivity of the surface of the electrodes 34, the surface area of the electrodes that contact the blood vessel wall may be selectively modified to facilitate focal delivery of electrical energy to a desired location.

Figure 4:
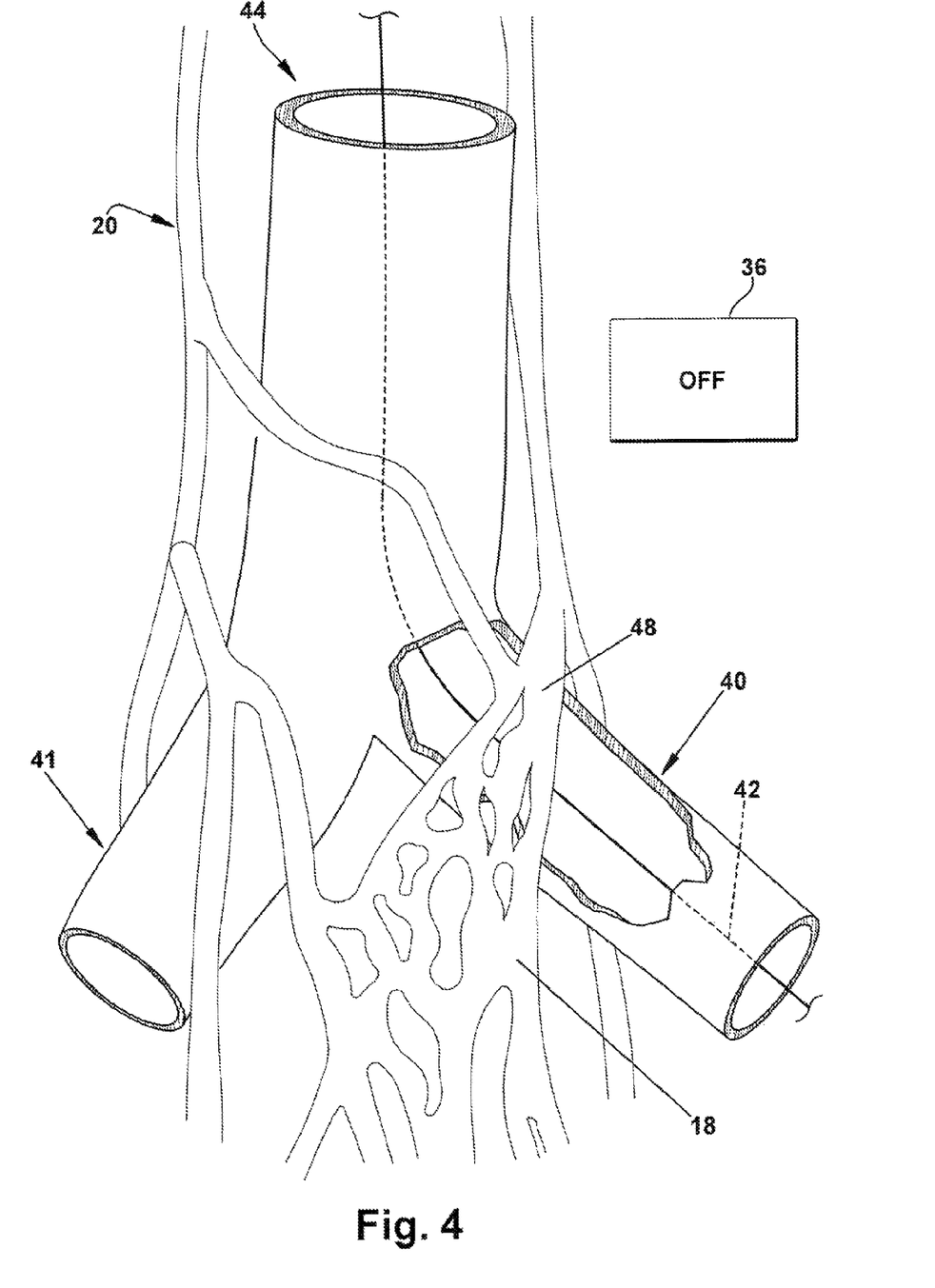
FIG. 4 is an exploded perspective view of the abdominal aorta in FIG. 3 showing a guidewire extending through the left femoral artery.
Figure 6:
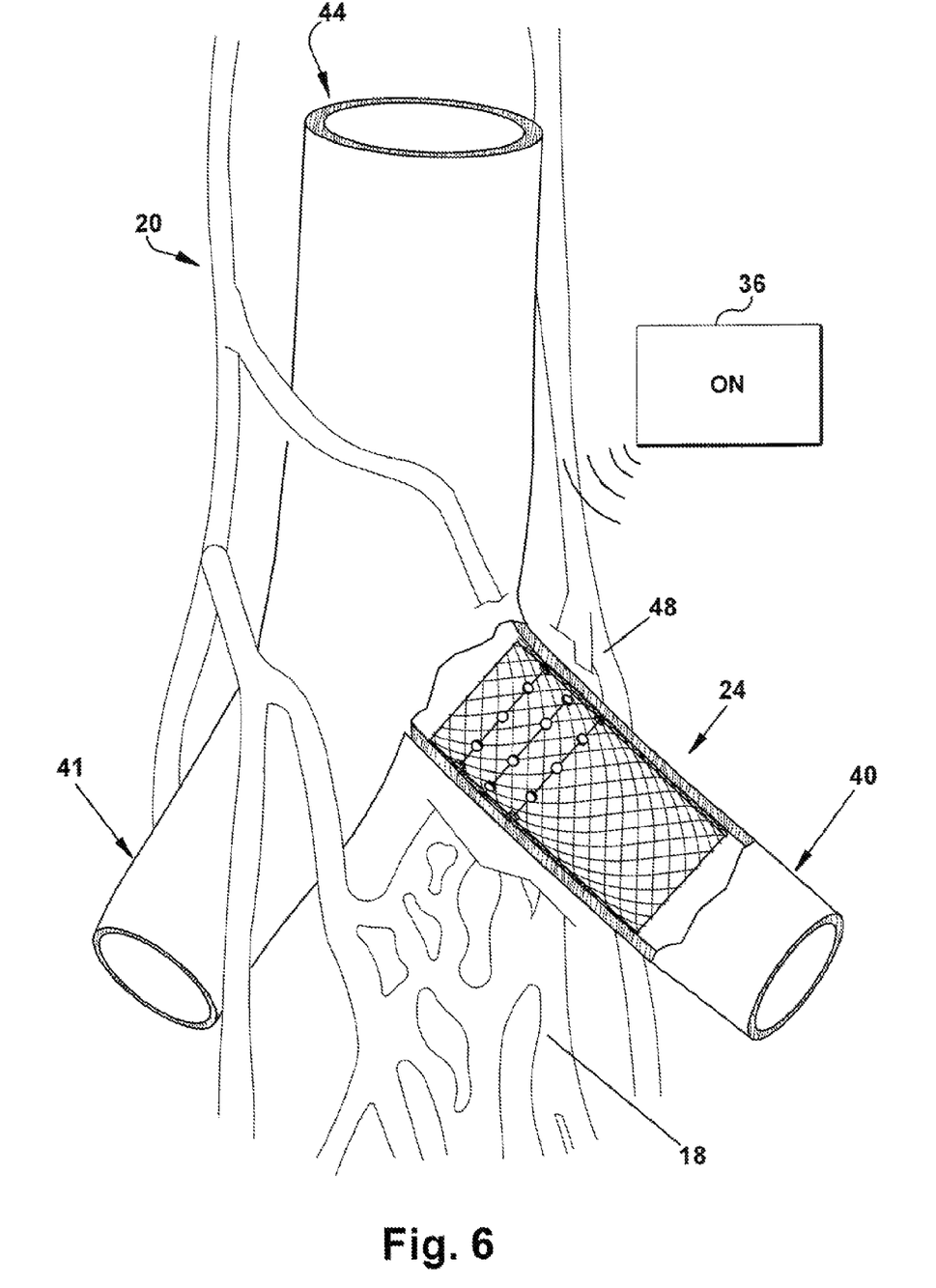
FIG. 6 is a perspective view of the expandable support member of FIG. 5 implanted in the left femoral artery.

Electrical energy can be delivered to the electrodes 34 using a variety of internal, passive, or active energy sources 36 (FIGS. 4-6). The energy source 36 may include, for example, radio frequency (RF) energy, X-ray energy, microwave energy, acoustic or ultrasound energy such as focused ultrasound or high intensity focused ultrasound energy, light energy, electric field energy, magnetic field energy, combinations of the same, or the like. Alternatively, the energy delivery source 36 can comprise a device capable of harvesting mechanical and/or thermodynamic energy from the body of a subject, such as a piezoelectric device.

The energy source 36 may be directly coupled to the expandable support member 24 using an electrical lead (not shown). The electrical lead may be disposed in an adjacent blood vessel and travel down the length of the adjacent vessel to a remote entry site (not shown). Alternatively, electrical energy may be supplied to the electrodes 34 via a turbine-like mechanism (not shown) operatively disposed in the lumen of the expandable support member 24. As blood flows through the lumen of the expandable support member 24, the turbine mechanism generates electrical energy which may then be delivered to the electrodes 34. Further, the energy source 36 may be wirelessly coupled to the expandable support member 24 as shown in FIGS. 4-6.

Electrical energy can be delivered to the electrodes 34 continuously, periodically, episodically, or a combination thereof. For example, electrical energy can be delivered in a unipolar, bipolar, and/or multipolar sequence or, alternatively, via a sequential wave, charge-balanced biphasic square wave, sine wave, or any combination thereof. Electrical energy can be delivered to all the electrodes 34 at once or, alternatively, to only a select number of desired electrodes. The particular voltage, current, and frequency delivered to the electrodes 34 may be varied as needed. For example, electrical energy can be delivered to the electrodes 34 at a constant voltage (e.g., about 0.1 v to about 25 v), at a constant current (e.g., at about 25 microampes to about 50 milliamps), at a constant frequency (e.g., at about 5 Hz to about 10,000 Hz), and at a constant pulse-width (e.g., at about 50 μsec to about 10,000 μsec).

Delivery of electrical energy to a select number of electrodes 34 may be accomplished via a controller (not shown), for example, operably attached to the expandable support member 24. The controller may comprise an electrical device which operates like a router by selectively controlling delivery of electrical energy to the electrodes 34. For example, the controller may vary the frequency or frequencies of the electrical energy being delivered to the electrodes 34. By selectively controlling delivery of electrical energy to the electrodes 34, the controller can facilitate focal delivery of electrical energy to a desired location. It should be appreciated that means other than electrical energy, such as chemical or biological means, may also be used.

Referring again to FIG. 3, the expandable support member 24 additionally comprises all insulative material 38 for isolating blood flow through the vessel from the electric current. More particularly, the insulative material 38 serves as an electrical insulator, separating electrical energy from blood flow and facilitating delivery of electrical energy to the vessel wall. The insulative material 38 is disposed radially inward of the electrodes 34 and extends along the entire length of the expandable support member 24. Alternatively, the insulative material 38 may be attached to select portions of the expandable support member 24, such as only the second end portion 28 and part of the main body portion 30. The insulative material 38 may be disposed between the electrodes 34 and the expandable support member 24 or, alternatively, disposed about the lumen of the expandable support member. The insulative material 38 generally has a low electrical conductivity and a non-thrombogenic surface. The insulative material 38 can include materials such as PTFE, ePTFE, silicone, silicone-based materials, and the like.

In addition to the insulative layer 38, at least a portion oldie expandable support member 24 may optionally include a layer (not shown) of biocompatible material. The layer of biocompatible material may be synthetic such as DACRON (Invista, Wichita, Kans.), GORE-TEX (W. L. Con. & Associates, Flagstaff, Ariz.), woven velour, polyurethane, or heparin-coated fabric. Alternatively, the layer of biocompatible material may be a biological material such as bovine or equine pericardium, peritoneal tissue, an allograft, a homograft, patient graft, or a cell-seeded tissue. The biocompatible layer can cover either the luminal surface of the expandable support member 24, the non-luminal surface of the expandable support member, or can be wrapped around both the luminal and non-luminal surfaces. The biocompatible layer may be attached around the entire circumference of the expandable support member 24 or, alternatively, may be attached in pieces or interrupted sections to allow the expandable support member to more easily expand and contract.

The expandable support member 24 can also include at least one wireless module (not shown) capable of receiving electrical energy for delivery to the electrodes 34. The wireless module may be operably coupled to the expandable support member 24 and may comprise an electrical device which operates like a router to selectively control delivery of electrical energy to the electrodes 34. For example, the wireless module may vary the frequency or frequencies of the electrical energy being delivered to the electrodes 34. By selectively controlling delivery of electrical energy to the electrodes 34, the wireless module can facilitate focal delivery of electrical energy to a desired location. Alternatively, the wireless module may passively distribute electrical energy to the electrodes 34.

Referring again to FIG. 1, the expandable support member 24 is implanted intravascularly at 14 so that at least a portion of the expandable support member is positioned substantially adjacent a desired location where modulation of the ANS is effective to treat ED. For example, the expandable support member 24 can be implanted at a desired location in an arterial or venous vessel. Alternatively, a first expandable support member 24 can be implanted intravascularly at a desired location in an arterial vessel and a second expandable support member can be implanted intravascularly at a desired location in a venous vessel. Further, first and second expandable support members 24 can be implanted intravascularly at separate desired locations in the same blood vessel.

Examples of suitable arterial vessels for intravascular implantation of the expandable support member 24 include, but are not limited to, an abdominal aorta, a femoral artery (a left femoral artery 40 or a right femoral artery 41), a common iliac artery, an internal iliac artery, an external iliac artery, a pudendal artery, an internal pudendal artery, and a gluteal artery. Examples of suitable venous vessels for intravascular implantation of the expandable support member include, but are not limited to, an inferior vena cava, a femoral vein, a common iliac vein, an internal iliac vein, an external iliac vein, a pudendal vein, an internal pudendal vein, and a gluteal vein.

The desired location(s) can comprise a variety of anatomical locations, including intraluminal and extraluminal locations innervated by at least one nerve. For example, the desired location an comprise an intravascular or extravascular location innervated by at least one nerve. Examples of desired locations according to the present invention include intravascular locations adjacent to and/or innervated by at least one of a sacral nerve or branches or portions thereof, a pudendal nerve or branches or portions thereof, a hypogastric nerve or branches or portions thereof, a superior hypogastric nerve or branches or portions thereof, an inferior hypogastric nerve or branches or portions thereof, a cavernous nerve or branches or portions thereof, an inferior mesenteric plexus or branches or portions thereof, a sympathetic chain nerve or branches or portions thereof, a prostatic plexus nerve or branches or portions thereof, a sacral splanchnic nerve or branches or portions thereof, a pelvic splanchnic nerve or branches or portions thereof, a prostate or branches or portions thereof, the pelvic floor, the penile dorsal nerve or portions thereof, the greater cavernous nerves or branches or portions thereof, the lesser cavernous nerves or branches or portions thereof, a prostatic plexus or branches or portions thereof, the pelvic splanchnic nerves or branches or portions thereof, the S1, S2, or S3 roots or branches or portions thereof or perineal nerves or branches or portions thereof.

After implanting the expandable support member 24 at a desired location, electric current is delivered to the electrodes 34 at 16 to modulate the ANS. As used herein, the term "modulate" or "modulating" refers to causing a change in neuronal activity, chemistry, and/or metabolism. The change can refer to an increase, decrease, or even a change in a pattern of neuronal activity. The term may refer to either excitatory or inhibitory stimulation, or a combination thereof, and may be at least electrical, biological, magnetic, optical or chemical, or a combination of two or more of these. The term "modulate" can also be used to refer to a masking, altering, overriding, or restoring of neuronal activity.

It will be appreciated by one having ordinary skill in the art that both the PNS and the SNS contribute to ED. As discussed above, for example, activation of the PNS leads to erection while activation of the SNS leads to detumescence. The PNS and SNS are not entirely antagonistic, however, as SNS activation is responsible for ejaculation. The present invention takes advantage of erectile neurophysiology by providing a method 10 for delivering electrical energy to the electrodes 34 of the expandable support member 24 to effect a change in the PNS, the SNS, or both, and thereby treat ED.

As shown in FIG. 1, electrical energy is delivered to the electrodes 34 at 16 to activate at least one nerve associated with the PNS at a desired location. Delivering electrical energy to at least one parasympathetic nerve associated with the target location will promote erection by triggering relaxation of penile smooth muscles and dilation the helicine arteries. Alternatively, electrical energy may be delivered to the electrodes 34 so that the PNS is activated to promote erection while simultaneously inhibiting or deactivating the SNS to prevent detumescence. Further, electrical energy may be delivered to the electrodes 34 to inhibit or deactivate the SNS and thereby prevent detumescence while allowing for normal PNS activity i.e., erection). Still further, where the PNS is first activated, electrical energy may be subsequently delivered to the electrodes 34 to activate the SNS and thus cause ejaculation.

In an example of the method 10, the expandable support member 24 can be intravascularly implanted at 14 as shown in FIGS. 4-6. Percutaneous placement of the expandable support member 24 starts by accessing a bodily vessel, such as the left femoral artery 40, with a delivery device. As shown in FIG. 4, a guidewire 42 is introduced into the vasculature via a vascular opening or incision (not shown). The guidewire 42 is inserted through the incision into the left femoral artery 40 in an antegrade direction and then urged into the abdominal aorta 44 as shown in FIG. 4.

Next, the expandable support member 24 is placed in a delivery catheter 46 in a collapsed configuration and securely attached to a proximal end (not shown) of the guidewire 42. The delivery catheter 46 is then advanced over the guidewire 42 as shown in FIG. 5. The delivery catheter 46 is advanced until the delivery catheter is suitably positioned, substantially adjacent a desired location in the left femoral artery 40. As shown in FIG. 5, the first end portion 26 of the expandable support member 24, which has a focal arrangement of electrodes 34, is positioned substantially adjacent a portion of the superior hypogastric plexus 48.

Once the expandable support member 24 is appropriately positioned in the left femoral artery 40, the delivery catheter 46 is removed and the constraining hands 32 are progressively released (i.e., broken) by the radial force generated by the self-expanding expandable support member. When all of the constraining bands 32 have been released, the expandable support member 24 obtains the expanded configuration and is securely positioned in the left femoral artery 40. With the expandable support member 24 securely positioned in the left femoral artery 40, the guidewire 42 is then removed from the vasculature.

Next, electrical energy, such as RF energy is delivered to the electrodes 34 via a wirelessly coupled energy source 36 as shown in FIG. 6. As electrical energy is delivered to the electrodes 34, the electrodes conduct electrical current to the vascular all at the desired location and thereby cause at least one parasympathetic nerve associated with the superior hypogastric plexus 48 to fire action potentials. The action potentials are then relayed to the hypogastric plexus 18, through the interior hypogastric plexus, and finally to the cavernous nerve where the smooth muscles of the penis relax and thereby cause an erection.

An electrical stimulus regimen comprising a desired temporal and spatial distribution of electrical energy to a desired location may be selected to promote efficacy of the present invention. It is theorized that uninterrupted or otherwise unchanging delivery of electrical energy to a desired location may result in associated nerves becoming less responsive over time, thereby diminishing long-term effectiveness of the therapy. Therefore, the electrical stimulus regimen may be selected to activate, deactivate, or otherwise modulate the ANS in such a way that therapeutic efficacy is maintained for a desired period of time.

In addition to maintaining therapeutic efficacy over time, the electrical stimulus regimen may be selected to reduce the power requirement/consumption of the expandable support member 24. For example, the electrical stimulus regimen may dictate that the expandable support member 24 be initially activated at a relatively higher energy and/or power level, and then subsequently activated at a relatively lower energy and/or power level. The first level attains the desired initial therapeutic effect, and the second (lower) level sustains the desired therapeutic effect long term. By reducing the energy and/or power levels after the desired therapeutic effect is initially attained, the energy required or consumed by the expandable support member 24 may also be reduced.

It should be appreciated that unwanted collateral stimulation of adjacent tissues may be limited by creating localized cells or electrical fields (i.e., by limiting the electrical field beyond a desired location). Localized cells may be created by, for example, spacing the electrodes 34 very close together or biasing the electrical field with conductors (not shown) and/or magnetic fields. For example, electrical fields may be localized or shaped by using electrodes 34 with different geometries, by using one or more multiple electrodes, and/or by modifying the frequency, pulse-width, voltage, stimulation waveforms, paired pukes, sequential pulses, and or combinations thereof.

It should also be appreciated that more than one expandable support member 24 may be used to modulate the ANS and this treat erectile dysfunction. For example, it may be desirable to modulate the hypogastric plexus 18 via an electrical field by placing a first expandable support member 24 in the left femoral artery 40 and a second expandable support member in the internal pudendal artery to modulate the pudendal nerve (not shown). With this arrangement, it may be possible to inhibit or deactivate the SNS with the first expandable support member 24 while stimulating or activating the PNS with the second expandable support member.

Figure 7:
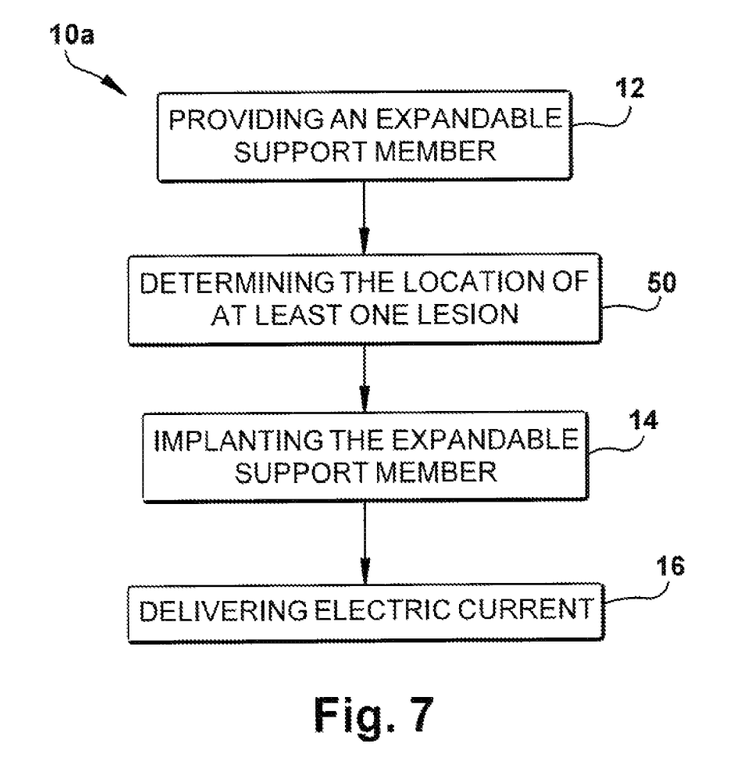
FIG. 7 is a process flowchart illustrating an alternative embodiment of the present invention.

Another embodiment of the present invention is illustrated in FIG. 7. In FIG. 7, a method $10_a$, is provided for treating neurogenic ED in a subject. The method $10_a$, is identical to the method 10 illustrated in FIG. 1, except where as described below. In FIG. 7, steps that are identical to steps in FIG. 1 use the same reference numbers, whereas steps that are similar but not identical carry the suffix "a".

Neurogenic ED can occur as the result of a lesion to a nerve or nerves associated with erectile function. For example, lesions which result from diabetes, spinal cord injury, multiple sclerosis, herniated discs, and surgery (e.g., radical prostatectomy, perineal prostatectomy, and abdominal resection), for example, may cause neurogenic ED.

To treat neurogenic ED according to the present invention, an expandable support member 24 is provided at 12 (as described above) and the location of at least one lesion causative of neurogenic ED is then determined at 50. The location of the lesion may be determined using any one or combination of known diagnostic imaging modalities including, for example, X-ray, ultrasound, MRI, CT, and fluoroscopy. Other types of non-imaging modalities, such as nerve conduction studies and motor skill assessment, may also be used to determine the location of the lesion.

After determining the location of the lesion using MRI, for example, the expandable support member 24 is implanted intravascularly at 14 (as described above) at a desired location where modulation of the ANS is effective to improve erectile function. One having ordinary skill in the art will appreciate that intravascular placement of the expandable support member 24 will depend, at least in part, on the type and location of the lesion. Where the lesion is a result of diabetes, for example, the expandable support member 24 may be implanted intravascularly at a desired location distal from the lesion. Alternatively, where the lesion is a result of a spinal cord lesion or aneurysm surgery, the expandable support member 24 may be implanted intravascularly at a desired location proximal to the lesion. Additionally, where the lesion is a result of a radical prostatectomy, for example, the expandable support member 24 may be implanted intravascularly at a desired location at or near the lesion.

After implanting the expandable support member 24 at the desired location, electric current may be delivered to the electrodes 34 at 16 to effect a change in the ANS (as described above). For example, electrical energy may be delivered to the electrodes 34 to activate at least one parasympathetic nerve associated with the desired location. Delivering electrical energy to at least one parasympathetic nerve associated with the desired location will promote erection by relaxing the smooth muscles of the penis and dilating the helicine arteries. Alternatively, electrical energy may be delivered to the electrodes 34 so that the PNS is activated to promote erection while simultaneously inhibiting or deactivating the SNS to prevent detumescence. Further, electrical energy may be delivered to the electrodes 34 to inhibit or deactivate the SNS and thereby prevent detumescence while allowing for normal PNS activity (i.e., erection). Still further, where the PNS is first activated, electrical energy may be subsequently delivered to the electrodes 34 to activate the SNS and cause ejaculation.

From the above description of the invention, those skilled in the art will perceive improvements, changes and modifications. It will be appreciated that various design and fabrication changes may be made to the expandable support member 24 depending upon the medical need(s) of the subject (e.g., the vascular anatomy of the subject or the type of lesion responsible for ED). For example, the expandable support member 24 may not include any insulative material 38. It will also be appreciated that the expandable support member 24 may be implanted using an open surgical procedure. Further, it will be appreciated that the expandable support member 24 may be implanted prophylactically following radical prostatectomy, for example. Such improvements, changes, and modifications are within the skill of the art and are intended to be covered by the appended claims.

Having described the invention, we claim:

1. A method for treating erectile dysfunction in a subject, said method comprising the steps of:

providing an expandable support member for engaging a wall of a blood vessel, at least one electrode being connected with the expandable support member and arranged to selectively deliver an electric current regimen to modulate the autonomic nervous system (ANS), and an insulative material attached to the expandable support member for isolating blood flowing through the vessel from the electric current regimen delivered by the at least one electrode;

implanting the expandable support member intravascularly so that at least a portion of the expandable support member is positioned substantially adjacent a desired location selecting an electric current regimen comprising a desired temporal and spatial distribution of electrical energy to the desired location to modulate the ANS to improve erectile function;

delivering the electric current regimen to the at least one electrode to modulate the ANS; and improving erectile function.

2. The method of claim 1, wherein at least a portion of the expandable support member is positioned at an intravascular location adjacent at least one of a sacral nerve or branches or portions thereof, a pudendal nerve or branches or portions thereof a hypogastric nerve or branches or portions thereof, a superior hypogastric nerve or branches or portions thereof, an inferior hypogastric nerve or branches or portions thereof, a cavernous nerve or branches or portions thereof, an inferior mesenteric plexus or branches or portions thereof, a sympathetic chain nerve or branches or portions thereof, a prostatic plexus nerve or branches or portions thereof a sacral splanchnic nerve or branches or portions thereof, a pelvic splanchnic nerve or branches or portions thereof a prostate or branches or portions thereof, the pelvic floor, the penile dorsal nerve or portions thereof, the greater cavernous, nerves or branches or portions thereof, the lesser cavernous nerves or branches or portions thereof, the S1, S2, or S3 roots or branches or portions thereof, perineal nerves or branches or portions thereof, or a combination thereof.

3. The method of claim 1, wherein at least a portion of the expandable support member is positioned substantially adjacent a desired location in an arterial vessel.

4. The method of claim 3, wherein at least a portion of the expandable support member is positioned substantially adjacent a desired location in an arterial vessel selected from the group consisting of an abdominal aorta, a femoral artery, a common iliac artery, an internal iliac artery, an external iliac artery, a pudendal artery, an internal pudendal artery, and a gluteal artery.

5. The method of claim 1, wherein at least a portion of the expandable support member is positioned substantially adjacent a desired location in a venous vessel.

6. The method of claim 5, wherein at least a portion of the expandable support member is positioned substantially adjacent a desired location in a venous vessel selected from the group consisting of an inferior vena cava, a femoral vein, a common iliac vein, an internal iliac vein, an external iliac vein, a pudendal vein, an internal pudendal vein, and a gluteal vein.

7. The method of claim 1, wherein two or more expandable support members are implanted intravascularly in different desired blood vessels.

8. The method of claim 7, wherein the two or more expandable support members are implanted in different desired arterial vessels.

9. The method of claim 7, wherein the two or more expandable support members are implanted in different desired venous vessels.

10. The method of claim 7, wherein at least one expandable support member is implanted at a desired location in an arterial vessel and at least one expandable support member is implanted at another desired location in a venous vessel.

11. The method of claim 1, wherein delivering the electric current regimen to the at least one electrode to modulate the ANS comprises effecting a change in the parasympathetic nervous system (PNS).

12. The method of claim 11, wherein effecting a change in the PNS comprises increasing PNS activity.

13. The method of claim 12, wherein increasing PNS activity comprises causing an erection.

14. The method of claim 1, wherein delivering the electric current regimen to the at least one electrode to modulate the ANS comprises effecting a change in the sympathetic nervous system (SNS).

15. The method of claim 14, wherein effecting a change in the SNS comprises decreasing SNS activity.

16. The method of claim 15, wherein decreasing SNS activity comprises substantially preventing detumescence.

17. The method of claim 1, wherein delivering the electric current regimen to the at least one electrode to modulate the ANS comprises decreasing SNS activity and increasing PNS activity.

18. The method of claim 17, wherein decreasing SNS activity comprises substantially preventing detumescence and increasing PNS activity comprises causing an erection.

19. The method of claim 1, further comprising chemically inducing a change in the ANS by at least one pharmacological agent associated with the expandable support member.

20. The method of claim 1, further comprising biologically inducing a change in the ANS by at least one biological agent associated with the expandable support member.

21. The method of claim 1, wherein delivering the electric current regimen to the at least one electrode to modulate the ANS comprises modulating neurohormonal activation.

* * * * *